(12) United States Patent
Geir et al.

(10) Patent No.: US 8,225,665 B2
(45) Date of Patent: Jul. 24, 2012

(54) METHOD AND SYSTEM OF MEASURING MATERIAL LOSS FROM A SOLID STRUCTURE

(75) Inventors: Instanes Geir, Nestun (NO); Mads Andre Toppe, Ulset (NO); Peter B. Nagy, Cincinnati, OH (US)

(73) Assignee: Clampon AS, Laksevag (NO)

( * ) Notice: Subject to any disclaimer, the term of this patent is extended or adjusted under 35 U.S.C. 154(b) by 766 days.

(21) Appl. No.: 12/227,805

(22) PCT Filed: May 30, 2007

(86) PCT No.: PCT/NO2007/000182
§ 371 (c)(1),
(2), (4) Date: Feb. 19, 2009

(87) PCT Pub. No.: WO2007/139389
PCT Pub. Date: Dec. 6, 2007

(65) Prior Publication Data
US 2009/0235748 A1    Sep. 24, 2009

(30) Foreign Application Priority Data

May 30, 2006  (NO) .................................. 20062464

(51) Int. Cl.
*G01B 17/02* (2006.01)
(52) U.S. Cl. ......................................... 73/597; 73/602
(58) Field of Classification Search .................... 73/597, 73/602, 622, 627, 620
See application file for complete search history.

(56) References Cited

U.S. PATENT DOCUMENTS

| 6,148,672 | A | 11/2000 | Cawley |
| 6,360,609 | B1 * | 3/2002 | Wooh ............................... 73/602 |
| 7,171,854 | B2 * | 2/2007 | Nagashima et al. ............ 73/622 |
| 2003/0033870 | A1 | 2/2003 | Shah |
| 2004/0221652 | A1 | 11/2004 | Flora |
| 2004/0255678 | A1 | 12/2004 | Nagashima |

OTHER PUBLICATIONS

Leonard, K.R. et al: "Lamb Wave Tomography of Pipe-like Structures", Ultrasonics vol. 43, pp. 574-583, Jun. 1, 2005.
Sargent, J.P.: "Corrosion Detection in Welds and Heat-Affected Zones using Ultrasound Lamb Waves", Insight vol. 48, No. 3, Mar. 2003.
Matt, H. et al: "Ultrasonic Guided Wave Monitoring of Composite Wing Skin-to-spar Bonded Joints in Aerospace Structures", J. Acoust. Soc. Am. 118(4), Oct. 2005, pp. 2240-2252.

* cited by examiner

*Primary Examiner* — J M Saint Surin
(74) *Attorney, Agent, or Firm* — Francis C. Hand; Carella Byrne Bain

(57) ABSTRACT

A method is described for measuring an amount of loss of material thickness from a solid structure in which acoustic waves can propagate. The structure is in operation in contact with substances susceptible to changing a thickness of the structure. A system operable to implement the method is also described. The system comprises acoustic transducers arranged in operation in contact with a surface of the solid structure. The system comprises a processing unit operable to drive one or more of the transducers to excite acoustic signals in a wall of the structure. The acoustic signals travel a distance within the structure and are received at the transducers to generate corresponding received signals for the processing unit to process and analyze. The analysis enables a degree of material loss from the structure to be computed and then optionally displayed on a display unit. The acoustic signals correspond to various modes and the processing unit (3) is operable to isolate signal components in the received signals, which provide a more reliable indication of the degree of material loss from the structure.

16 Claims, 7 Drawing Sheets

METHOD AND SYSTEM OF MEASURING MATERIAL LOSS FROM A SOLID STRUCTURE

FIELD OF THE INVENTION

The present invention relates to methods of measuring material loss, for example to a method of measuring an amount of loss of material thickness from a solid structure in which acoustic waves propagate in operation, the structure being in contact with one or more substances susceptible to changing a thickness of the structure: Moreover, the present invention also concerns systems operable to implement such methods, for example to a system comprising a plurality of acoustic transducers arranged in contact with a surface of a solid structure, a processing unit coupled to the acoustic transducers for transmitting signals thereto and receiving signals therefrom and for analysing the received signals for computing a degree of material loss from the structure, and optionally a display unit coupled to the processing unit for presenting measurement results indicative of the degree of material loss.

BACKGROUND OF THE INVENTION

In many industrial processes, there are encountered hostile substances that need to be transported through flow conduits or stored in containers. Such substances can exhibit corrosive and/or erosive properties when interacting with their environment. There is therefore a need for systems and methods that over a duration of time are operable to monitor an impact of such corrosion and/or erosion in order to ensure safe operation of associated conduits or containers.

During production of oil and natural gas, such hostile substances consist of oil, water, gas, in many cases different amounts of sand, and also different chemical additives. Pressures and temperatures of the hostile substances are normally high and security for safe operation over a period of years is imperative. Therefore, there is a need for an accurate and robust measurement system that is operable to monitor parameters as a thickness of a wall of a conduit, since this thickness will certainly change over time. It is not sufficient to measure this thickness at a single location of a pipe or a conduit. Larger portions of the pipe or conduit must be monitored as well, and for this purpose the present invention has shown its effectiveness.

A thickness assessment procedure pertinent to the present invention comprises a comprehensive analysis of phase and group velocity dispersion characteristics of appropriate propagation modes of an acoustic signal utilized to implement the procedure. A choice of modes for the analysis constitutes an important issue when implementing the procedure, as not all modes are equally sensitive to variations in wall thickness.

However, a technical problem is that concomitant complications arising owing to mode overlapping and distortion have to be tackled and overcome for the procedure. Long term thickness monitoring necessarily has to face a fact that local thickness variations potentially comprise a significant percentage of a corresponding average wall thickness; most guided wave modes do not display a sufficient degree of robustness required to smoothly integrate these variations into a quantitative thickness assessment.

Other systems are known which seek to address a similar technical problem to that of the present invention. A first known method and system typically utilizes pulsed acoustic signals over larger distances of greater than 2 meters, and analyzes reflected echoes from such pulsed acoustic signals in order to determine a presence of material damage. Moreover, the reflected signal echoes are susceptible to providing an indication of a location and an approximate spatial extent of the material damage, but are not able to provide quantitative information about an average wall thickness reduction.

A second method and system in contemporary use is capable of performing spot measurements at a position whereat transducers are located on a pipe. In the second method and system, pure longitudinal transverse resonances of zero group velocity (ZGV) are readily exploited for performing local thickness measurements implemented in a pulse-echo mode of operation. Averaging the thickness measurements at several different locations whereat transducers are mounted on the pipe are used to obtain valuable information on the nominal average thickness of the pipe if the longitudinal velocity is known, or to estimate the longitudinal velocity from initial measurements on a calibration pipe of known wall thickness. This second method is only able to provide a very local estimate of pipe wall thickness, but is not able to give necessary information about an average wall thickness over a larger part of the pipe. If the wall thickness were changing more or less uniformly over a distance between the transducers, one could just average thicknesses measured at the different transducer locations. However, long-range inspection necessarily has to face a problem that an average of the two thicknesses measured at ends of a given inspection path is not representative to a true average between those two ends.

A third method and system involves utilizing a so-called 'Low Group Velocity' (LGV) measurements between one or more pairs of acoustic transducers, and analyzing a family of longitudinal and shear waves that travel at such lower regime group velocities along a path for obtaining an estimate of general wall thickness condition therealong. These low group velocity measurements are extremely sensitive to uneven variations in wall thickness along the aforesaid path of propagation; the measurements can be exploited to flag paths where uneven variations are detected.

Theoretical analyses, as well as practical applications, have shown that an LGV-based assessment breaks down when there are local thickness variations in an order of 10% of an absolute wall thickness of a pipe section, when these defects occupy a reasonable percentage of a line-of-sight between transducers involved for implementing the assessment. The LGV method is thus capable of providing an overall assessment of the 'well being' of the pipe section. Partly due to the curvature of the pipe section and partly to a divergence of an ultrasonic beam produced by the finite-aperture transducers, some ultrasonic energy will also be radiated sideways and will consequently be lost from an otherwise perfect standing wave generated. This sideways radiation represents a principal damping of transverse resonance and also is the source of propagating Lamb modes. Among these propagating Lamb modes are modes of particular interest that allow a natural extension of the aforesaid ZGV method to a pitch-catch mode of operation. LGV modes represent both shear and longitudinal bulk waves bouncing back and forth between surfaces of a plate at close to normal incidence; in consequence, the resulting transverse resonance frequencies include two families of dominantly shear and longitudinal vibration, respectively.

The LGV method is highly sensitive to wall thickness variations over a propagation path between transducers involved, wherein such sensitivity badly limits a feasibility of this otherwise very simple LGV method for performing long-range inspection. The LGV technique exhibits a problem, like other techniques that are very sensitive to wall thickness variations, that it is not able to average at all the wall thickness between a transmitter and a receiver employed to implement the method because of a very non-linear relationship between measured propagation parameters and the sought wall thickness. The LGV method produces sharp transmission peaks in its corresponding transmitted spectrum, which can be associated with shear and longitudinal transverse resonances. For example, a 10 mm thick pipe produces, among others, a distinct transmission peak at a frequency of ≈600 kHz that gradually increase to a frequency of ≈680 kHz in response to the wall thickness reducing to 9 mm. However, if there is a step down from a wall thickness of 10 mm to a thinner wall thickness of 9 mm, a thicker part of the pipe transmits therethrough ultrasonic energy at frequencies that are not transmitted through the thinner part, therefore the transmission peak does not shift to a new position between frequencies of 600 and 680 kHz, but simply disappears. Such disappearance occurs irrespective of whether such a step change is gradual rather than localized; a tapered section from 10 mm at one end to 9 mm at the other of a section of pipe would not transmit ultrasonic energy therethrough pertaining to a simple LGV method.

SUMMARY OF THE INVENTION

An object of the present invention to provide a system and method which overcome the above-mentioned contemporary measurement problems.

The present invention thus relates to a method and a system, wherein the system is operable to implement the method. The system is fitted onto a surface of a suitable solid structure, for example a fluid carrying pipe or a container, containing substances that can have an impact on a thickness of a wall of the solid structure due to for instance corrosion or erosion. Moreover, the system is also fitted in other situations wherein data related to a loss of wall thickness needs to be determined and evaluated. Especially in a case of dynamic pipeline monitoring, a measurement system necessarily has to face extremely hostile conditions of operation including surface roughness, fluid loading issues, temperature variations, and a host of other factors that make development of a robust wall thickness assessment tool a challenging task.

The method and system described herein is used as a part of an online, real-time path based thickness assessment tool; the tool involves deployment of a set of transducers working in pairs over a given pipe length and thereby also pipe area, and utilizes principles of guided wave dispersion to quantify loss of wall thickness over time. The method is characterized in that a pulsing transducer is operable to transmit a pre-determined acoustic signal, which is later received by a receiving transducer. Successive signals of this sort are compared and mathematically differentiated to correlate signal change as a function of wall thickness loss. The system utilizes a unique method of analyzing received acoustic waves and quantifying an amount of wall loss from measured dispersion of the received acoustic waves.

The method and the measuring system in accordance with the invention described herein involves measurement of certain characteristics of acoustic Lamb waves generated in a solid material in order to determine a thickness of the solid material and more specifically changes in such material thickness over time. The solid material preferably has properties for rendering it possible for acoustic Lamb waves to propagate therein; more specifically, the solid material may be a steel pipe containing flowing fluids wherein such fluid over time generates corrosion and/or erosion of a pipe wall of the pipe. The solid material is optionally also a part of a container or tank containing one or more fluids.

The acoustic Lamb waves are susceptible to being generated between pairs of two acoustic transducers working in pitch-catch mode and which are mounted with a certain distance between them onto the surface of the solid material. The method is characterized as being a Constant Group Velocity (CGV) method wherein a specific mode of the acoustic signal having an approximately constant group velocity over a certain frequency range is isolated by a gating technique. The phase velocity of this specific mode is susceptible to being highly dispersive over the same frequency range and it changes in a systematic way with changes in the thickness of the solid material. By measuring the phase angle of this signal, the material thickness can be determined.

The method enables the average material thickness to be determined on-line, in real time, and over a rather longer distance of the solid material.

The method and system described herein is unique in comparison to other techniques utilized for monitoring wall thickness of objects such as pipelines, conduits in general, and containers. No other systems utilize permanently installed ultrasonic transducers that use dispersion properties of guided waves to quantify an amount of wall loss between sensors over a larger distance along a structure.

The method and system pursuant to the present invention involves employing acoustic modes that provide maximum sensitivity to changes in wall thickness within constraints imposed by a necessary robustness which the method and system need to exhibit in operation. In other words, the presence of highly localized damage and defects is quantitatively incorporated into a robust average thickness measurement, such measurement employing an effective spectral and temporal dispersive analysis of generated and received signal waveforms Practical laboratory trials conducted pursuant to the method indicate a sensitivity of less than 1% of average wall thickness to changes in this quantity, in the presence of local thickness changes that are of an order of magnitude larger. Clearly, spurious effects, such as losses due to fluid loading, apparent reduction in sensitivity due to surface roughness, the presence of epoxy coatings, and temperature swings are all important factors that affect the system, but these have all been fully investigated and accounted for. The robustness of the dispersion based method developed has been found to be crucial for reducing otherwise critical effects; a reduced net error is thereby achievable.

DESCRIPTION OF THE DRAWINGS

Embodiments of the invention will now be described, by way of example only, with reference to the accompanying drawings wherein.

DETAILED OF EMBODIMENTS OF THE INVENTION

Figure 1:
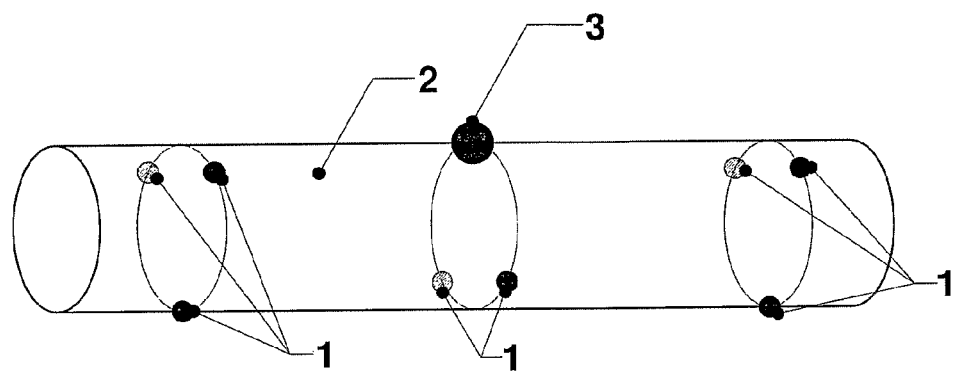
FIG. 1 is a schematic diagram of one configuration of acoustic transducers clamped onto an outer surface of a pipe.

Ultrasonic guided waves are well suited for long-range inspection of pipelines and other solid structures. In relatively thin-walled pipes, such guided waves can be approximated as Lamb modes propagating along helical paths that allow the same mode to arrive at a receiver at different times. However, there are several orders of these modes and the propagation length of the n-th order helical path around a cylindrical pipe is described by Equation 1 (Eq. 1) below $$l_n = \sqrt{z^2 + (a+2\pi nR)^2} \qquad \text{Eq. 1}$$

Here, parameters z and a are axial and azimuthal distances between the transmitter and receiver respectively, and a parameter R is an average radius of the pipe, and n is the azimuthal order.

Although higher-order modes are more affected by a circumferential curvature of the pipe, in thin-walled pipes their velocity is essentially the same as for a zero-order mode that follows a most direct path between a transmitter and a receiver and all modes can be crudely approximated by a corresponding Lamb mode in a flat plate.

However, because of a highly dispersive nature of these Lamb modes, fast modes following a helical path can actually beat slower modes following a more direct route, therefore an observed vibration at a location of a receiver is much more complicated than one would assume based on direct Lamb wave propagation only. On account of such complexity, a lagging part of a direct signal (n=0) that interferes with earliest arrivals along longer helical paths must be disregarded when evaluating the detected signal using a simplistic Lamb wave approximation. Higher azimuthal orders (n≠0) can be even stronger than the direct arrival (n=0) when a=0, so that positive and negative first-order modes arrive simultaneously and mutually constructively interfere. At sufficiently low frequencies, it is to be appreciated that only a fundamental asymmetric mode can propagate in the pipe. Another possible mode, namely a fundamental symmetric mode, produces almost entirely tangential surface displacement, and therefore cannot be effectively generated and detected by longitudinal contact transducers.

Although actual velocities are somewhat different, especially for higher-order helical modes, because of the curvature of the tube, experimentally observed arrivals are in good agreement with values expected from the aforesaid simple Lamb mode approximation. Most importantly, these typical arrival times clearly indicate that proper care must be taken, either not to include the higher-order helical modes in the gated signal, or by taking into consideration an interference of these signals with the direct arrival signal. Since both the phase and group velocities of dispersive modes are dependent on frequency, quantitative evaluation of data necessitates spectral analysis of a received signal in order to be able to compare it to known dispersion curves of different Lamb modes that might propagate in the pipe.

A low frequency asymptotic velocity ($c_p$) of the lowest order symmetric mode, corresponding to a dilatational wave propagating in a thin plate, is a fastest possible group velocity in the plate at low frequencies; it therefore represents an earliest arrival, which can be easily identified even though the first arrival is usually far from the strongest of all signals present. In aforesaid calculations, longitudinal and shear bulk velocities were assumed to be $c_d$=5,900 m/s and $c_s$=3,200 m/s, which corresponds to a thin-plate velocity of $c_p$=5,377 m/s; Poisson's ratio is taken to have an approximate value of 0.29. Very often, transducers used to generate and detect Lamb waves are themselves sensitive to a given phase velocity $c_{ph}$. For example, when an angle-beam transducer is employed, independent of the frequency, a probe thereby provided is selectively sensitive to a narrow phase velocity range as approximately given by Equation 2 (Eq. 2):

$$c_{ph} = \frac{c_{wedge}}{\sin\theta_{wedge}}, \qquad \text{Eq. 2}$$

wherein $c_{wedge}$ is a longitudinal velocity in a wedge and $\theta_{wedge}$ is an angle of incidence. In other words, all excited modes lie on a horizontal line corresponding to this longitudinal velocity. Conversely, electromagnetic acoustic transducers with a meandering coil of periodicity ($\Lambda$) are selectively sensitive to given wavelengths ($\lambda$) that are integer multiples of the coil periodicity. For the strongest coupling wherein $\Lambda=\lambda$, allowed phase velocities lie on a straight line with a given slope as defined by Equation 3 (Eq. 3):

$$c_{ph}=f\Lambda. \qquad \text{Eq. 3}$$

In an inspection system pursuant to the present invention, longitudinal contact transducers are used, and therefore no specific sensitivity to a certain phase velocity is expected. However, constructive interference over an entire aperture of the transducer requires that its probe diameter (D) be equal or smaller than half the wavelength, namely as defined by Equation 4 (Eq. 4):

$$c_{ph} \geq 2fD. \qquad \text{Eq. 4}$$

If this condition is not satisfied, an expected Lamb wave spectrum will be badly distorted by not only the finite bandwidth of the transducer, but also its finite aperture. In most practical cases, the tube thickness and diameter are proportional to each other. Similarly, a ratio between a diameter of the applicable probe and the wall thickness (d) is also more or less constant. It is important to ensure sufficiently high phase velocities for D=d. Although the D≦λ/2 condition is arguably too restrictive for probes of circular apertures, a fact remains that in a region below this line, the received measured signal will be distorted by finite-aperture effects. These adverse effects are not corrected for in the system pursuant to the present invention, and therefore they lead to additional uncertainties in the assessment of the aforesaid wall thickness. An interesting range for the assessment described herein is a region over which a fundamental asymmetric (flexural) mode exhibits more or less constant group velocity (CGV) at about 60% relative to a first arrival corresponding to the propagation velocity $c_p$. This flexural mode lends itself readily for long-range pitch-catch measurements over a relatively wide frequency range since its group velocity is essentially constant; therefore an associated pulse can be easily separated from the rest of the signal by appropriate gating, while its phase velocity exhibits fairly strong dispersion, which allows it to be used for thickness assessment. This approach is somewhat less accurate than utilizing two transverse resonance methods previously described under prior art, but it smoothly integrates the wall thickness over a whole inspection length, therefore it is very robust and represents a best candidate for real-time erosion and corrosion monitoring in pipes.

In long-range guided wave measurements, a measured group time of arrival and phase angle are related to average group ($\bar{c}_{gr}$) and phase velocities ($\bar{c}_{ph}$), respectively. These average velocities can be calculated from Equation 5 (Eq. 5):

$$\frac{z}{\bar{c}_{gr}(m, f)} = \int_0^z \frac{dz}{c_{gr}(z; m, f)} \qquad \text{Eq. 5}$$

and $$\frac{z}{\bar{c}_{ph}(m, f)} = \int_0^z \frac{dz}{c_{ph}(z; m, f)},$$

wherein z is a propagation distance from a transmitter to a receiver. Here, it is assumed that wave guide properties, namely a wall thickness in the present example, change only gradually over distances many times larger than the wall thickness, therefore the Lamb modes do not scatter backwards or forwards into other types of modes and that the system is completely linear, namely signals of a given frequency do not produce any other frequencies; in other words, m and f can be regarded as constants. In such cases, it is customary to introduce a concept of slowness instead of velocity so that a process of averaging involved becomes linear. The slowness is defined simply as an inverse of velocity, therefore Equation 5 (Eq. 5) can be re-written as follows in Equation 6 (Eq. 6):

$$\bar{s}_{gr}(m, f) = \frac{1}{z}\int_0^z s_{gr}(z; m, f)\,dz \qquad \text{Eq. 6}$$

and $$\bar{s}_{ph}(m, f) = \frac{1}{z}\int_0^z s_{ph}(z; m, f)\,dz.$$

To better elucidate problems associated with averaging, it is advantageous to consider phase and group velocity dispersion curves in terms of slowness. Accurately measuring the average wall thickness as provided by Equation 7 (Eq. 7):

$$\bar{d} = \frac{1}{z}\int_0^z d(z)\,dz \qquad \text{Eq. 7}$$

over an extended propagation length clearly involves two contradictory requirements. On the one hand, sensitive detection of wall thickness variations requires a mode that is very sensitive to such variations, namely either phase or group slowness curves must be very steep. On the other hand, proper averaging requires that at a given frequency these velocities are more or less linear functions of a local wall thickness. For example, assuming that the phase velocity of a particular mode is a more or less linear function of thickness at a given frequency×thickness product($fd_m$), then Equation 8 (Eq. 8) pertains:

$$s_{ph} \approx s_0 + Sf(d - d_m), \qquad \text{Eq. 8}$$

wherein $s_0 = s_{ph}(f\,d_m)$ and S is a slope of a phase slowness diagram at that particular point. Using phase-sensitive detection, it is feasible to measure an average phase slowness pursuant to Equation 9 (Eq. 9):

$$\bar{s}_{ph} = s_0 + Sf(\bar{d} - d_m), \qquad \text{Eq. 9}$$

which can be readily solved for a sought average wall thickness ($\bar{d}$).

There are few modes that can be used to assess a true average of the varying wall thickness along the propagation path since most modes exhibit a highly nonlinear slowness curve. This is especially true for those modes that are most sensitive to wall thickness variations since steepest parts of pertinent dispersion curves tend to be also least linear over a substantial thickness range, for example over a range of ±10-20% One notable exception is the aforesaid constant group velocity (CGV) flexural mode.

In a next section of this description, the phase and group slowness dispersion curves for the constant group velocity (CGV) flexural mode will be further elucidated. In a vicinity of a highlighted point at $f \cdot d \approx 1.25$, the slowness is a fairly linear but still sufficiently sensitive function of a frequency× thickness product. This figure indicates that as much as 20-30% relative change in wall thickness can be tolerated without seriously compromising the reliability of an obtained average thickness value, a value that seems to be sufficient in most erosion and corrosion monitoring applications. The feasibility of using this technique for long-range average thickness assessment will be described in more detail later.

Based on analytical results, an only mode which offers a reasonable chance of success for quantitatively assessing an average wall thickness using long-range guided wave measurements is the low-frequency flexural mode in the constant group velocity (CGV) range where the phase velocity of the mode exhibits a more or less linear relationship with wall thickness. In order to concentrate a frequency distribution of a generated guided wave spectrum in the CGV range, a transmitter is beneficially driven with a signal with predetermined characteristics. Under such drive conditions, only fundamental symmetric and asymmetric modes are excited. Furthermore, both modes exhibit essentially non-dispersive and rather different ($\approx 40\%$) group velocities, therefore appropriate gating can relatively easily separate them. While the phase velocity of the symmetric mode is also fairly non-dispersive, the phase velocity of the asymmetric mode is highly dispersive, which is illustrated by a rapidly changing phase shift within a constant envelope of slower and stronger flexural pulses.

A fact that no significant scattering-induced attenuation occurs when the fundamental flexural mode propagates through a plate with varying thickness by itself is very promising for exploiting this mode for truly integrating long-range wall thickness assessment. A crucial issue is, however, whether or not the integrated phase delay can be used to characterize the average wall thickness, within some reasonable limits, for arbitrarily varying thickness profiles. As a first test, a simple case of transmission through a steel plate was studied, wherein the plate's thickness abruptly dropped from 10 mm to 9 mm at different locations along an inspection length thereby resulting in different values of a corresponding the average wall thickness. The phase over a center frequency band is practically flat since the group velocity is approximately constant, while the integrated phase is proportional to the average thickness regardless of whether the wall thickness is uniform or includes a 1-mm single step. As expected, a relationship between the phase angle and the wall thickness is slightly nonlinear, but the relationship is smoothly changing and monotonic, therefore it is also readily invertible.

Although a fairly good correlation can be observed between the actual average thickness and the total phase shift of the transmitted signal even in this case, the limitations of the technique are also visible. Whenever a modest change in the average wall thickness is due to a much larger, but highly localized change, for example in a case of a 4-mm-deep triangular groove in a 10 mm-thick pipe wall, the measured thickness will be lower than a true average pertaining thereto. Since the measured thickness is distorted from the true average, namely 9 mm in the example, towards the minimum thickness, namely 6 mm in the example, the estimate is conservative, namely there is predicted a lower than average value for very uneven wall thicknesses. Generally, the measured value will be reasonably close to the average value only when the largest wall thickness reduction is less than five times the average wall thickness reduction. It should be mentioned that larger, highly localized wall thickness reductions cannot be assessed by the integrating phase measurement method, but could possibly be characterized based on the overall reduction of the amplitude of the transmitted signal, or possibly using reflection measurements in pulse-echo mode.

When devising the present invention, seven spectra were investigated for seven different frequencies of a single-cycle excitation signal and in addition the measured phase spectra of the flexural signal were evaluated for three different excitation frequencies in a same steel pipe. These phase spectra were calculated by first minimizing their frequency slope over the relevant frequency range partly to determine a corresponding group delay and partly to independently measure the phase delay. Based on a roughly ±15° experimental uncertainty in phase measurement, an expectation was that the accuracy of the thickness assessment could be around ±1%, namely better than ±0.1 mm.

It is will be appreciated that one respect in which the present system has tremendous unexploited reserves is its speed of executing measurements. For erosion and corrosion monitoring purposes, the measuring time could be almost arbitrarily long, for example hours versus seconds or minutes, therefore extensive time averaging could be applied to recover weak signals from the surrounding electrical, and possibly mechanical and acoustical, noise when a transducer is driven far below its resonant frequency. Therefore, one important issue is that relatively high-frequency transducers are susceptible to being used to generate and detect the low-frequency signals so that frequency-dependent phase distortions in the transducers can be minimized at the expense of reduced sensitivity, namely a tradeoff which has no real detrimental effect on an accuracy and reliability of the overall thickness measurement method pursuant to the present invention.

As elucidated in the foregoing, an analysis technique pursuant to the present invention involves mathematically evaluating a fundamental flexural mode at a section of a dispersion curve whereat the group velocity of this mode is unchanged, and relating the change in phase velocity of this mode with changes in the average wall thickness. The following explicit nonlinear inversion formula Equation 10 (Eq. 10) was thereby derived:

$$d \approx \frac{1}{f}\left[a_0 + \frac{a_1}{F_0 - \frac{\Delta\Phi}{2\pi fz}} + \frac{a_2}{\left(F_0 - \frac{\Delta\Phi}{2\pi fz}\right)^2}\right], \quad \text{Eq. 10}$$

wherein $a_0 = -0.2963$, $a_1 = 0.157$, and $a_2 = -0.0013$, and $F_0$ can be calculated from Equation 11 (Eq. 11) as follows:

$$F_0 = \frac{a_1 + \sqrt{a_1^2 + 4(fd_0 - a_0)a_2}}{2(fd_0 - a_0)}. \quad \text{Eq. 11}$$

Here, d is a sought wall thickness in mm, $d_0$ is an initial baseline wall thickness in mm, $\Delta\Phi$ is a measured true phase angle change relative to an initial phase in radians, f is a centre frequency in MHz, and z is an inspection length in mm.

A following explicit nonlinear inversion formula Equation 12 (Eq. 12) was derived to improve the accuracy of the previous formula (Eq. 11):

$$d \approx \frac{c_d}{f}\left[e_0 + \frac{e_1}{G_0 - \frac{\Delta\Phi c_d}{2\pi fz}} + \frac{e_2}{\left(G_0 - \frac{\Delta\Phi c_d}{2\pi fz}\right)^2}\right], \quad \text{Eq. 12}$$

wherein $e_0 \approx -0.02834\zeta$, $e_1 \approx 0.08757\zeta$, $e_2 \approx -0.00523\zeta$, $\zeta = c_d/c_s$ and $G_0$ can be calculated from Equation 13 (Eq. 13):

$$G_0 = \frac{e_1 + \sqrt{e_1^2 + 4(fd_0/c_d - e_0)e_2}}{2(fd_0/c_d - e_0)}. \quad \text{Eq. 13}$$

Here, a parameter d is a sought wall thickness, a parameter $d_0$ is an initial baseline wall thickness, a parameter $\Delta\Phi$ is a measured true phase angle change relative to an initial phase in radians, a parameter f is a center frequency, and a parameter z is an inspection length.

Referring to FIG. 1, there is shown a schematic diagram of one example of a system comprising a layout of eight acoustic transducers 1 clamped onto an outer surface of a pipe 2. It should be noted that the system is not limited to this number of transducers 1, but that it can comprise at least one pair of such acoustic transducers 1, or any higher number of such transducers 1.

The transducers 1 work in pairs from time to time wherein one transducer 1 is used as a transmitter and a second transducer 1 receives the signal. Any of the transducers 1 can be used as transmitter and likewise any of the transducers 1 can also be used as receivers. The pipe 2 is a conduit for a corrosion or erosion generating substance flowing through therethrough and is also the conduit for transmission of acoustic signals. A centrally placed processing unit 3 is operable to collect signals from all the transducers 1, and is also operable to execute all necessary calculations and further is operable to transmit measured results thereby obtained to a unit for display and storage of data.

Figure 2:
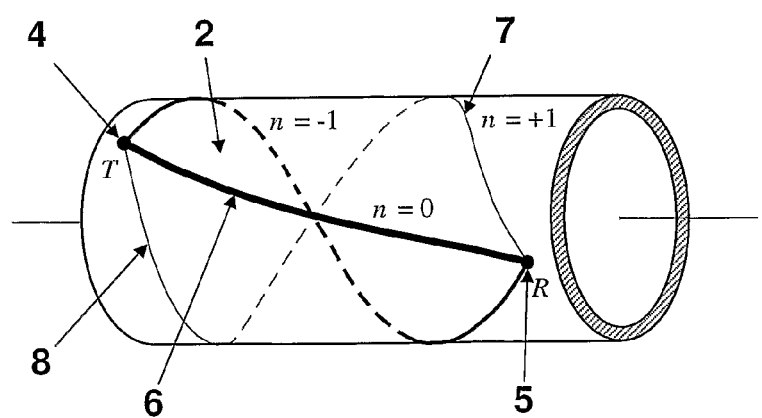
FIG. 2 is a schematic diagram of three lowest-order helical paths along and around a cylindrical pipe.
Figure 3:
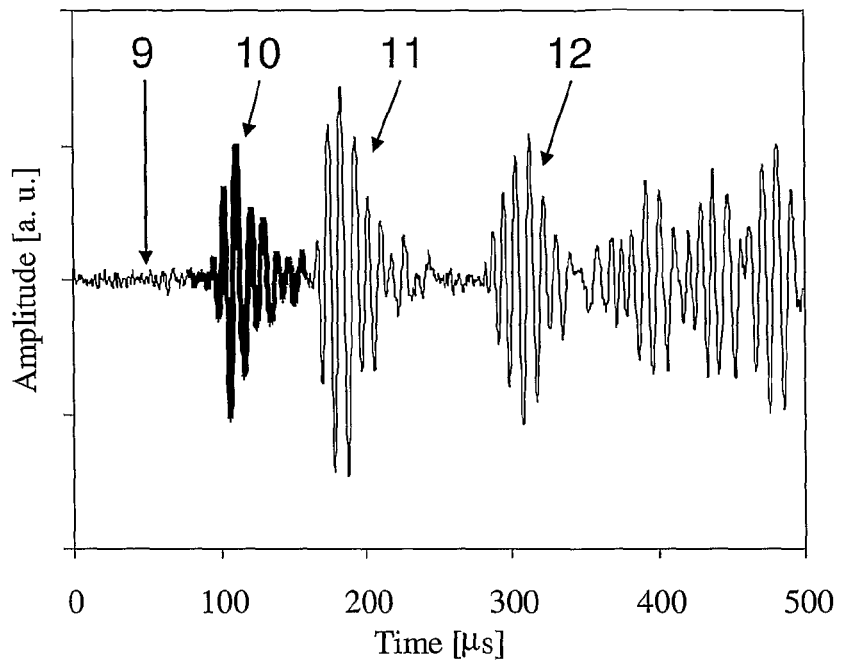
FIG. 3 is an illustration of a measured transmitted signal on a 143-mm-diameter, 6.2-mm-thick, 1200-mm-long steel tube for z=300 mm axial distance with no azimuthal offset (a=0)

Referring next to FIG. 2, there is shown a flow conduit, for example the aforementioned pipe 2 provided with two transducers, namely a transmitting transducer 4 and a receiving transducer 5. In addition, there is shown a path 6 of a directly arriving signal and two helical paths 7 and 8. These paths, 6, 7 and 8 illustrates three lowest-order paths along the cylindrical pipe 2. In FIG. 3, there is shown a measured transmitted signal 9 consisting of a response to a direct transmission 10 corresponding to the direct path 6, combined responses 11 to the two helical paths 7 and 8 and responses 12 to higher order helical paths.

Figure 4:
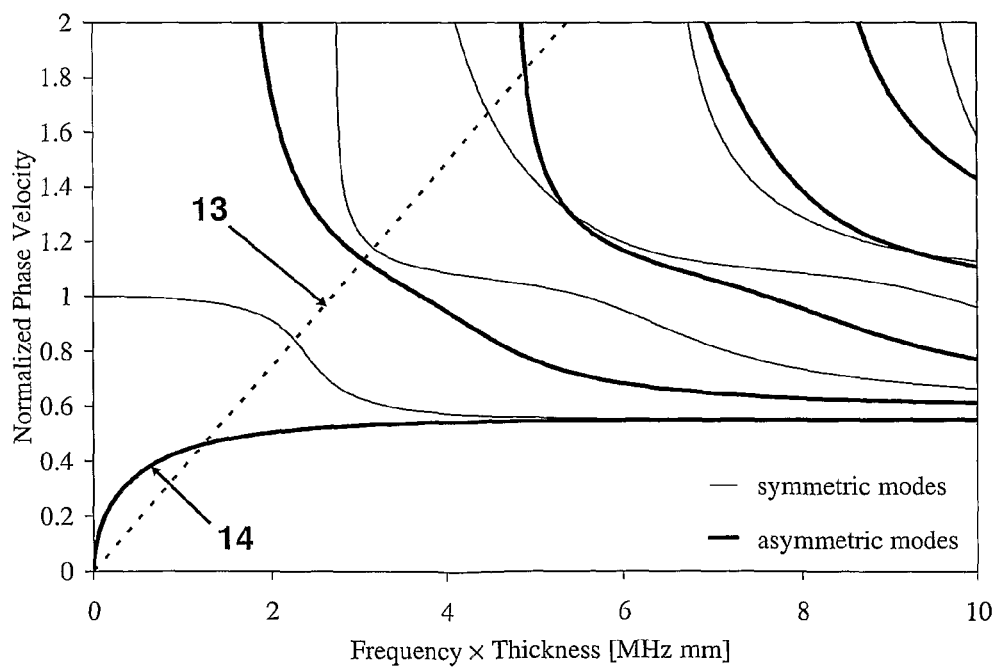
FIG. 4 is an illustration of phase velocity dispersion curves for Lamb waves propagating in a steel plate.

Referring next to FIG. 4, there is shown phase velocity dispersion curves for Lamb waves in a steel plate. An area above a straight line 13 represents sufficiently high phase velocities to ensure that a transducer diameter, D, is equal to or smaller than the wall thickness, d. A mode denoted by 14 is a mode which is most relevant for the system and the method described herein.

Figure 5:
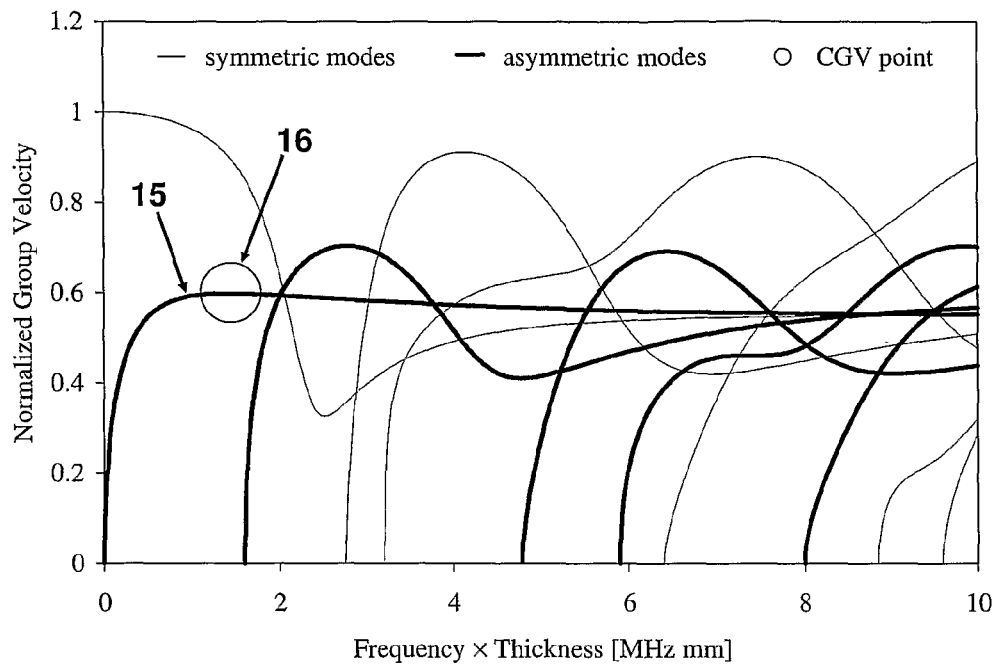
FIG. 5 is an illustration of group velocity dispersion curves for Lamb waves propagating in a steel plate, in particular CGV modes.
Figure 6:
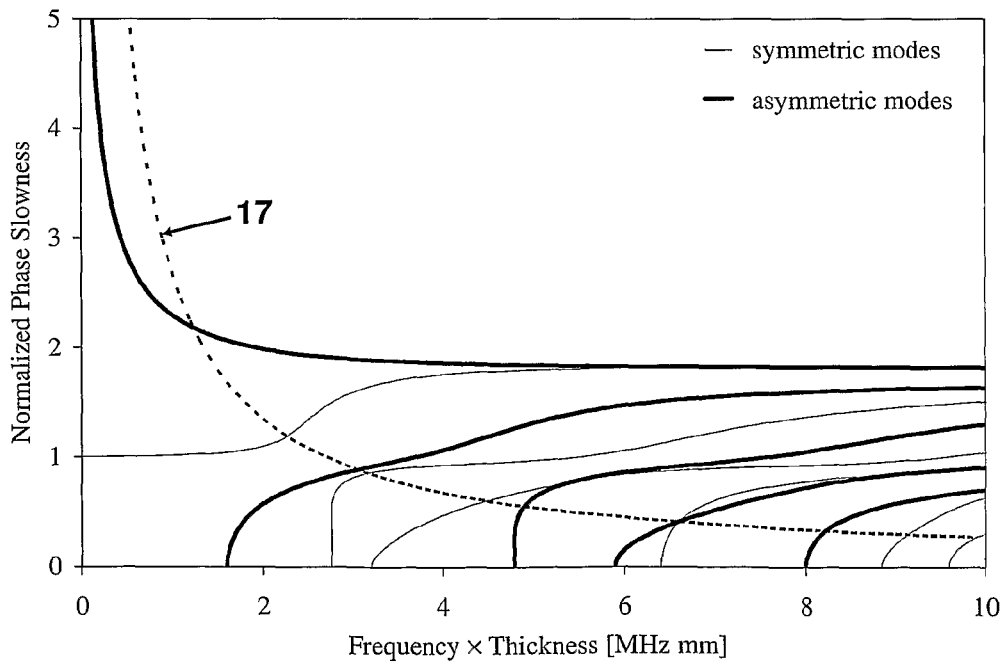
FIG. 6 is an presentation of phase slowness dispersion curves for Lamb waves propagating in a steel plate.

Referring to FIG. 5, there is shown corresponding group velocity dispersion curves for Lamb waves in a steel pipe, where a mode 15 is seen to have an approximately constant value independent of an associated frequency thickness product. An analysis of the constant group velocity mode is concentrated in a region 16 of the curves; in FIG. 6, there is shown the phase slowness dispersion curves for Lamb waves in a steel plate. An area below a curve 17 represents sufficiently high phase velocities to ensure that the transducer diameter, D, is equal to or smaller than the wall thickness, d.

Figure 7:
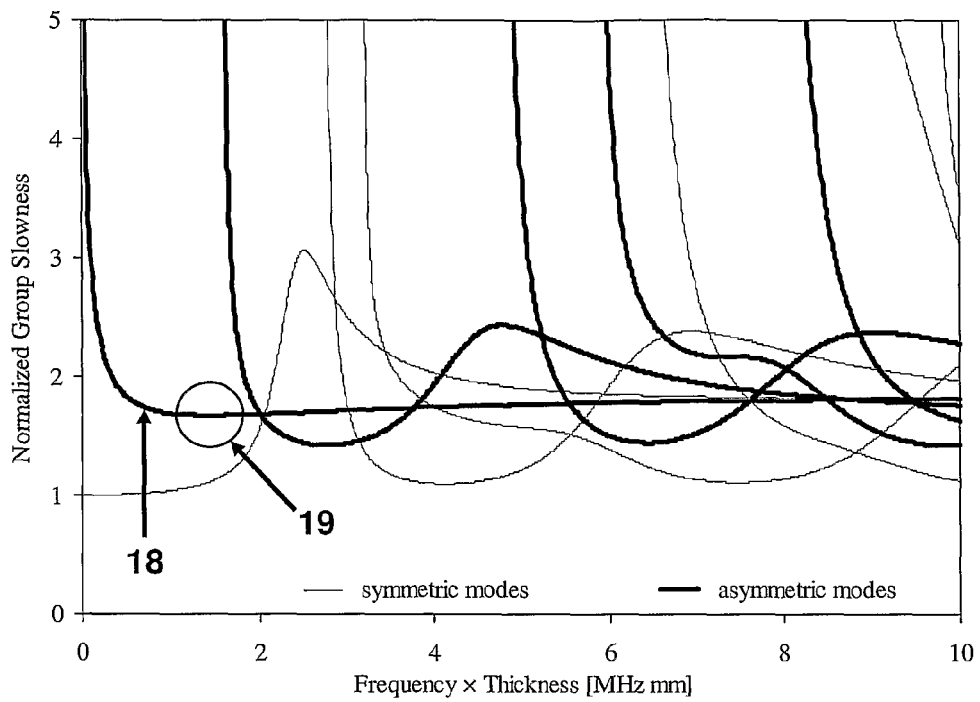
FIG. 7 is a presentation of group slowness dispersion curves for Lamb waves propagating in a steel plate, in particular the aforesaid CGV modes.

In FIG. 7, there is shown the group slowness dispersion curves for Lamb waves in a steel plate where a constant group velocity mode 18 is shown together with a region 19 of interest for the analysis described herein.

Figure 8:
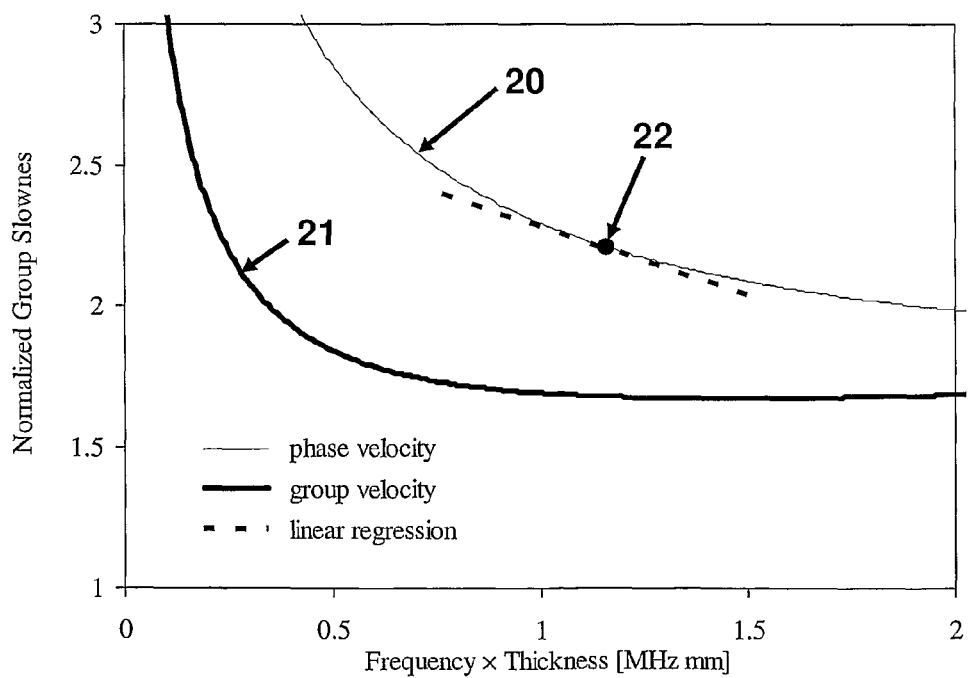
FIG. 8 is a presentation of the phase and group slowness dispersion curves plotted together for the constant group velocity (CGV) flexural mode.

In FIG. 8, there is shown two curves of particular interest, namely phase 20 and group 21 slowness dispersion curves for the constant group velocity (CGV) flexural mode. At a highlighted point 22 at a frequency×thickness product of 1.25 MHz mm, the slowness is fairly linear, but still a sufficiently sensitive function of the frequency×thickness product.

Figure 9:
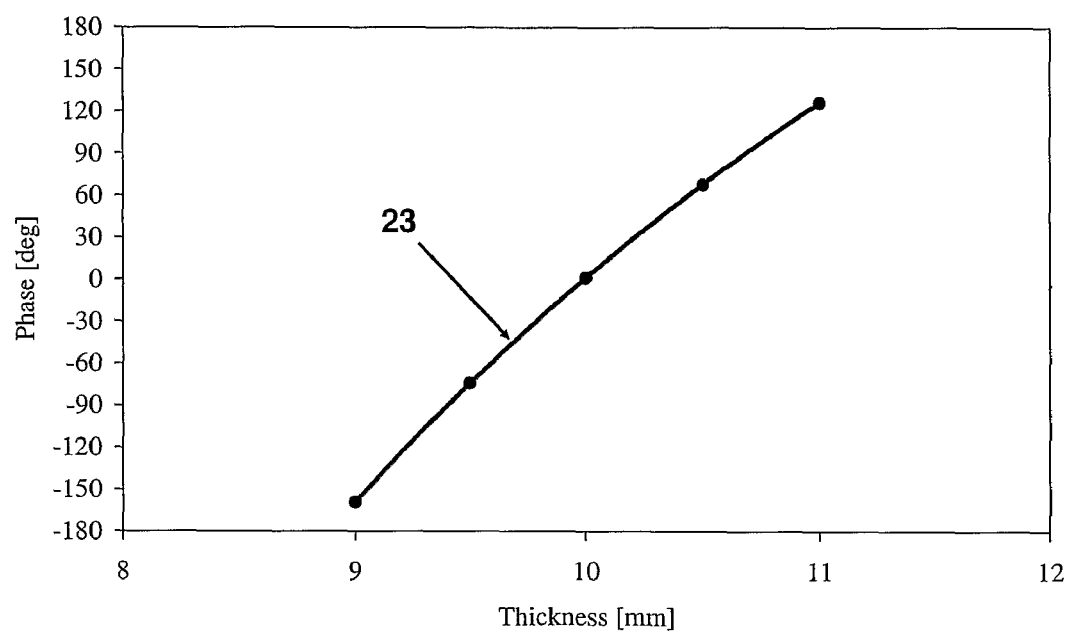
FIG. 9 is a presentation of the phase angle of a flexural pulse at its nominal center frequency for different wall thicknesses.

In FIG. 9, there is shown a calculated phase angle 23 of the flexural mode for different wall thicknesses at a nominal centre frequency. As expected, based on FIG. 8, a relationship between phase angle and wall thickness is not quite linear, but smooth and monotonic. Therefore, the relationship can be easily inverted to assess the sought wall thickness from the measured phase angle.

Figure 10:
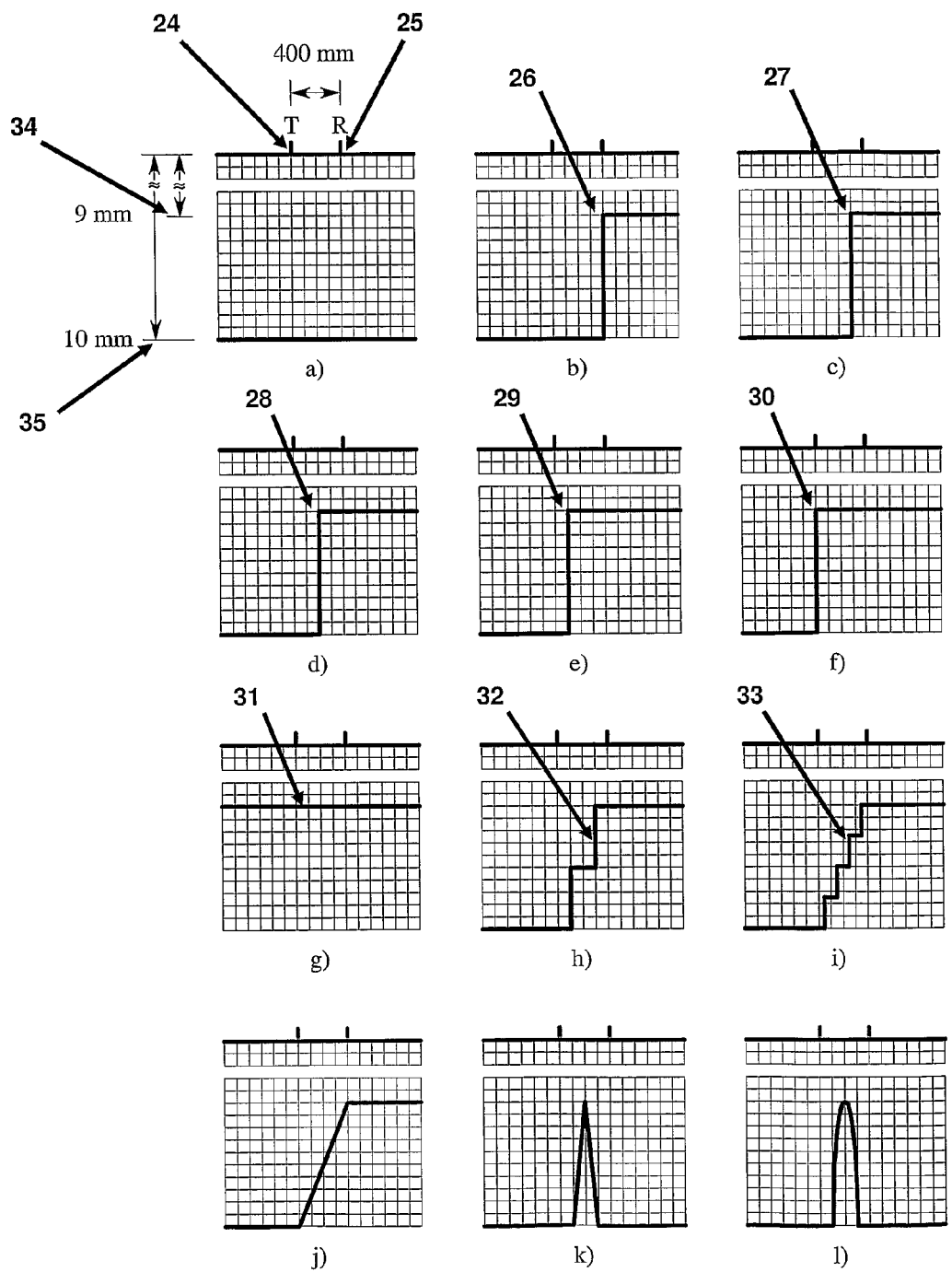
FIG. 10 is an illustration of various thickness profiles used in numerical simulations of the measurement method pursuant of the present invention.

In FIG. 10, there are illustrated several different changes of the wall thickness related to the position of transmitting 24 and receiving 25 transducers. In particular, there are shown abrupt single steps of wall thickness from 10 mm (denoted by 34) to 9 mm (denoted by 35). Referring to FIG. 10 b), there is shown a 100% single step denoted by 26 where the average wall thickness between the transducers 24 and 25 is 10.0 mm. Referring to FIG. 10 c), there is shown a 75% single step denoted by 27 whereat the average wall thickness between the transducers 24 and 25 is 9.75 mm. In FIG. 10 d), there is shown a 50% single step denoted by 28 whereat the average wall thickness between the transducers 24 and 25 is 9.50 mm. In FIG. 10 e), there is shown a 25% single step denoted by 29 where the average wall thickness between the transducers 24 and 25 is 9.25 mm. Referring to FIG. 10 f), there is shown a 0% single step denoted by 30 whereat the average wall thickness between the transducers 24 and 25 is 9.0 mm. In FIG. 10 g), there is shown a uniform wall thickness 31 of 9.0 mm between the transducers 24 and 25. Nest, in FIG. 10 h), there is shown a double-step denoted by 32 whereat the average wall thickness between the transducers 24 and 25 is 9.50 mm. Referring to FIG. 10 i), there is shown a quadruple-step 33 whereat the average wall thickness between the transducers 24 and 25 is 9.50 mm.

Figure 11:
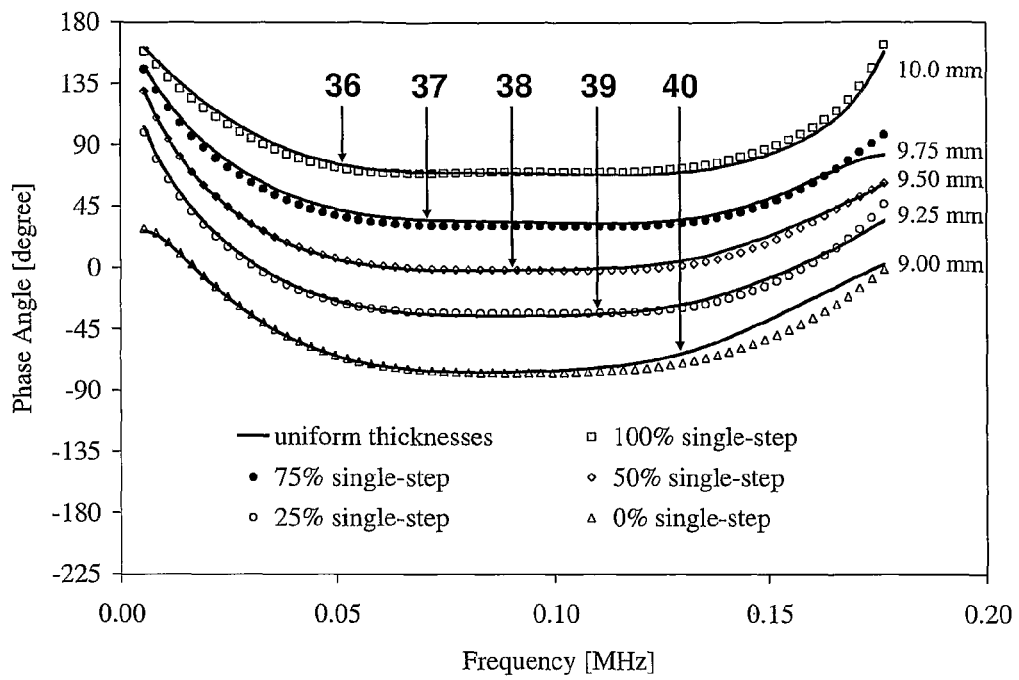
FIG. 11 is an illustration of the phase angle spectra of a fundamental flexural mode for different uniform wall thicknesses and uneven thickness profiles with a single step.

In FIG. 11, there is shown the phase angle versus frequency for the fundamental flexural mode for different uniform wall thicknesses and uneven thickness profiles. A curve 36 represents a phase angle for a 10.0 mm wall thickness of a 100% step, such step corresponding to the step 26 of FIG. 10 b). A curve 37 represents the phase angle for a 9.75 mm wall thickness of a 75% step, such step corresponding to the step 27 of FIG. 10 c). A curve 38 represents the phase angle for a 9.5 mm wall thickness of a 50% step, such step corresponding to the step 28 of FIG. 10 d). A curve 39 represents the phase angle for a 9.25 mm wall thickness of a 25% step, such step corresponding to the step 29 of FIG. 10 e). A curve 40 represents the phase angle for a 9.0 mm wall thickness of a 0% step, such step corresponding to the step 30 of FIG. 10 f).

Figure 12:
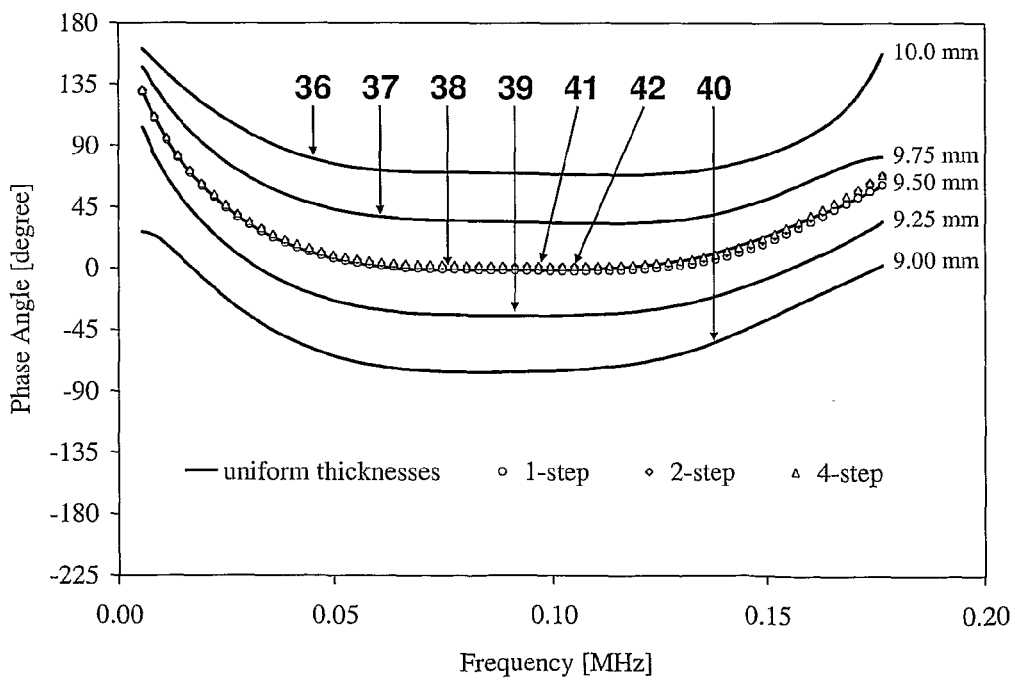
FIG. 12 is an illustration of the phase angle versus frequency for uniform thickness, denoted by solid lines, and uneven thickness, denoted by symbols, of the same 9.5 mm average wall thickness.

FIG. 12 shows similar curves 36, 37, 38, 39 and 40 to those shown in FIG. 11, but in addition three different geometries for an average wall thickness of 9.5 mm. These three different geometries are, again, the single step illustrated as the step 28 in FIG. 10 d), and in addition to a double step 32 as in FIG. 10 h) and a quadruple-step 33 as in FIG. 10 i). The resulting measured phase angle curves 41 and 42 are identical to the curve 38. The curves 41 and 42 show that the system and method described herein are capable of determining the average wall thickness independent of which physical form the wall thickness reduction takes. The change in wall thickness was caused by 1, 2, or 4 equal steps evenly distributed over the inspection length.

The invention claimed is:

1. A method of measuring an amount of loss of material thickness from a solid structure operable to support propagation of acoustic waves therein, said method comprising the steps of
    (a) placing a plurality of acoustic transducers in contact with a surface of the solid structure;
    (b) transmitting an acoustic signal from at least one of the plurality of acoustic transducers into a wall of said structure, and receiving the transmitted acoustic signal at a plurality of said transducers after travelling a distance within the solid structure;
    (c) collecting signals from said plurality of said transducers in a processing unit;
    (d) analyzing and comparing the received signals generated in step (b) and/or with results from earlier corresponding measurements, wherein the signal received by the receiving acoustic transducer and analyzed in the processing unit is a fundamental asymmetric (flexural) mode generated by the one or more transmitting acoustic transducers, wherein signal components corresponding to said flexural mode are isolated from signal components of other modes by using a gating technique applied to the received signals and wherein the processing unit analyzes a group velocity and a phase velocity of said flexural mode in a range wherein a group velocity of said flexural mode is approximately constant, said processing unit computing from a change in the said phase velocity a change in a true thickness of the solid structure; and
    (e) computing a degree of loss of material thickness from said solid structure from an analysis executed in step (d).

2. A method as claimed in claim 1, characterized in that said method comprises a further step of sending processed data from step (d) and/or step (e) computed in the processing unit to a display unit for displaying said degree of loss of material thickness.

3. A method as claimed in claim 1 or 2, characterized in that the signals received by the transducers and analysed in the processing unit correspond to propagation modes excited by one or more of the transducers, and wherein components of said propagation modes are isolated from components of other modes in said signals by utilizing differences between modes arising as a result of their respective propagation speeds in said solid structure.

4. A method as claimed in claim 1, characterized in that said method includes a step of starting with a baseline waveform reading and comparing subsequent waveforms to said baseline waveform reading for quantifying reductions in the true thickness of said solid structure.

5. A method as claimed in any one of claims 1, 2, 3 and 4, characterized in that said processing unit is operable when analysing the signals received at the transducers to compute an average reduction of a true wall thickness within an area of the solid structure.

6. A method as claimed in any one of claims 1, 2, 3, 4 and 5, characterized in that the solid structure is a pipe operable to carry a flowing fluid consisting of at least one flow constituent.

7. A method as claimed in any one of claims 1, 2, 3, 4, 5 and 6, characterized in that the signals received by the one or more receiving acoustic transducers and analyzed in the processing unit includes signals components corresponding to any of higher n-th order acoustic propagation modes generated by one or more of the transmitting acoustic transducers.

8. A method as claimed in claims 1, 2, 3, 4, 5, 6 and 7, characterized in that said processing unit is operable to apply corrections for a loss in sensitivity relating the phase angle to wall thickness of said solid structure due to curvature of the solid structure, such curvature including wall thickness to conduit diameter ratio and conduit bends in an axial direction along said solid structure.

9. A system for measuring a degree of loss of material thickness from a solid structure operable to support propagation of acoustic waves therein, said system comprising
   a plurality of acoustic transducers arranged in contact with a surface of the solid structure, and
   a processing unit for exciting one or more of said transducers (1) and for receiving signals therefrom for analysis, wherein a plurality of said transducers are disposed for exciting acoustic signals in a wall of the solid structure, and a plurality of said transducers are disposed for receiving the transmitted acoustic signals after travelling a distance within the solid structure, wherein the received signals from said transducers are subsequently sent to said processing unit for analysis therein for mutual comparison and/or for comparison with corresponding earlier signals for computing a degree of material loss from said solid structure;
   wherein said processing unit when analysing said signals received at said plurality of transducers is operable to isolate signal components corresponding to a flexural mode excited by said plurality of transmitting acoustic transducers, said signal components corresponding to said flexural mode being isolated from signal components of other modes by applying a signal gating technique to the received signals in the processing unit; and
   wherein said processing unit is operable to analyze a group velocity and a phase velocity of said fundamental flexural mode in a range wherein the group velocity of said flexural modes is approximately constant, said analysis being used to detect a change in said phase velocity and therefrom compute a change in a true thickness of said solid structure.

10. A system as claimed in claim 9, characterized in that said system further comprises a display unit coupled to said processing unit for receiving analysis data therefrom for displaying said degree of material loss from said structure.

11. A system as claimed in claim 9 or 10, characterized in that said processing unit is operable to compute from sensed changes in acoustic properties of said structure changes in a true average thickness of the solid structure over a distance the acoustic signals have propagated between the plurality of transducers.

12. A system as set forth in any one of claims 9 to 11 wherein said processing unit is operable to analyse said received signals by commencing with a baseline waveform reading and then comparing subsequent waveforms to said baseline waveform reading for quantifying reductions in a true thickness of the solid structure.

13. A system as set forth in any one of claims 9 to 11 and 12 wherein said system is operable to determine and/or quantify an average reduction of a true wall thickness along paths in the solid structure in which said acoustic signals propagate.

14. A system as set forth in any one of claims 9 to 11, 12 and 13 wherein said processing unit is mounted onto a surface of the solid structure.

15. A system as set forth in any one of claims 9 to 11, 12, 13 and 14 wherein the solid structure is a pipe operable to carrying a flowing fluid consisting of at least one flow constituent.

16. A system as set forth in any one of claims 9 to 11, 12, 13, 14 and 15 wherein the signal received by a respective one of said receiving acoustic transducers and analyzed in the processing unit corresponds to one or more n-th order acoustic propagation modes excited by one or more of the transmitting acoustic transducers.

* * * * *